United States Patent
Arshintseva et al.

(12)

(10) Patent No.: US 11,383,870 B2
(45) Date of Patent: Jul. 12, 2022

(54) THERMAL METHOD FOR STERILIZING POLOXAMER COMPRISING LIQUID DRUGS

(71) Applicants: Elena Valentinovna Arshintseva, Saransk (RU); Sergei Yurevich Pushkin, Noginsk (RU)

(72) Inventors: Elena Valentinovna Arshintseva, Saransk (RU); Sergei Yurevich Pushkin, Noginsk (RU)

( * ) Notice: Subject to any disclaimer, the term of this patent is extended or adjusted under 35 U.S.C. 154(b) by 287 days.

(21) Appl. No.: 16/637,276

(22) PCT Filed: Jul. 12, 2018

(86) PCT No.: PCT/RU2018/000460
§ 371 (c)(1),
(2) Date: Feb. 7, 2020

(87) PCT Pub. No.: WO2020/013725
PCT Pub. Date: Jan. 16, 2020

(65) Prior Publication Data
US 2020/0247570 A1    Aug. 6, 2020

(51) Int. Cl.
| | | |
|---|---|---|
| *B65B 55/14* | (2006.01) | |
| *A61L 2/00* | (2006.01) | |
| *B65B 3/00* | (2006.01) | |

(52) U.S. Cl.
CPC ............ *B65B 55/14* (2013.01); *A61L 2/0023* (2013.01); *B65B 3/006* (2013.01); *A61L 2202/21* (2013.01); *B65B 2220/24* (2013.01)

(58) Field of Classification Search
CPC ..... B65B 55/14; B65B 3/006; B65B 2220/24; B65B 7/2821; A61L 2/0023; A61L 2202/21; A61L 2/07
See application file for complete search history.

(56) References Cited

U.S. PATENT DOCUMENTS 8,617,467 B2    12/2013 Rodriguez et al.

FOREIGN PATENT DOCUMENTS

| RU | 2157241 C2 * | 10/2000 |
| RU | 2157241 C2 | 10/2000 |
| RU | 2392004 C2 | 6/2010 |
| RU | 2393849 C2 | 7/2010 |

OTHER PUBLICATIONS

N.N. Melnikovskaya, N.K. Krylova, "Parenteralnoe Belkovoe Pitanie I Novye Krovezameniteli", uchebno-metodicheskoe posobie, 1977, p. 112, Moscow.

\* cited by examiner

*Primary Examiner* — Sean E Conley
*Assistant Examiner* — Brendan A Hensel

(57) ABSTRACT

The invention relates to chemical and pharmaceutical industry, in particular to technologies of obtaining sterile drugs, drug substances and cosmetic products used in the form of solutions or emulsions, and comprising poloxamer. The thermal method for sterilizing aqueous poloxamer solutions is provided, the method including: dissolving a poloxamer in water for injection; performing the sterilizing filtration of the aqueous poloxamer solution simultaneously with filling sterile containers with the filtered poloxamer solution; sealing the containers containing the poloxamer solution; applying a thermal sterilization with steam under pressure to the containers containing the poloxamer solution, and cooling them, wherein the thermal sterilization of the containers containing the poloxamer solution with steam under pressure is performed under the pressure between 82.4 and 107.8 kPa.

10 Claims, No Drawings

THERMAL METHOD FOR STERILIZING POLOXAMER COMPRISING LIQUID DRUGS

The invention relates to chemical and pharmaceutical industry, in particular to technologies of obtaining sterile drugs, drug substances and cosmetic products used in the form of solutions or emulsions, and comprising poloxamer.

Poloxamers relate to standard nonionogenic surfactants for liquid pharmaceutical products. Commercial poloxamers are known under the following trade names: Proxanol, Emuxol, Kolliphor, Pluronic, Synperonic, Lutrol. Under certain conditions, these polymers can form a gel in a water recipe. These gel forming properties appear at a certain temperature.

Typically, solutions of poloxamers, particularly solutions that contain only 10% of a polymer, look like a low-viscous liquid. The temperature of a gel formation point clearly depends on the concentration of a poloxamer in an aqueous solution: the higher the concentration of the poloxamer, the lower the temperature of the gel formation point. The inverse relation was established for the strength of the gel formed: the strength of the gel was higher for higher concentrations of the poloxamer. Furthermore, adding a poloxamer, for example diclofenac, into an aqueous solution increases the gel formation temperature, while adding sodium chloride, on the contrary, reduces it.

Gel formation is a problem when a thermal sterilization method is implemented with steam of solutions containing a poloxamer since the sterilization temperature varies around 120° C. which is 2-3 times higher than the gel formation temperature and typically leads to irreversible appearance of a gel in a solution with a poloxamer.

A number of inventions are provided to solve this problem.

Known is a method for purifying proxanols by removing foreign impurities that determine their pyrogenicity such as degraded microorganisms and products of their vital activity of polysaccharide, oligo- or polypeptide and oligonucleotide nature (H. H. Мельниковская, Н. К. Крылова, "Парентеральное белковое питание и новые кровезаменители", под ред. О. К. Гаврилова. Moscow, 1977, p. 112). According to the method, dry proxanol is dissolved in pyrogen-free water to a concentration of 10-15%, then the solution is treated with activated charcoal in a stirred tank reactor, the treated solution is filtered through sterilizing asbestos filters to remove the coal, and the resulting solution of proxanol is lyophilized.

This method allows purifying proxanols to the apyrogenic state. However, the nanoimpurities of the coal dust that are incorporated into micelles of 10-20 nm formed by the poloxamer generally can not be removed by using only the sterilizing filtration method, and this can cause side effects when drugs containing such poloxamers are intravenously administered.

Known is a method described in the RU patent No. 2393849, wherein a poloxamer solution or a mixture of different poloxamers is purified by passing through a carbon sorbent and a sterilizing filter under the pressure of an oxygen-free gas, the solution is heated for 8-24 hours and cooled to 16-20° C. to completely recover the transparency of the solution, the aqueous solution is heated at a temperature that is selected within the range of ±2° C. of the cloud point established experimentally for the resulting mixture of poloxamers.

This method does not overcome the disadvantages of the previous method, and the long heating of the poloxamer solution that doesn't include the step of thermal sterilization with steam under pressure (autoclaving) at the cloud point does not ensure the sterilization and depyrogenation of the solution. Sterility of a solution is achieved only by sterilizing filtration.

Known is a method described in U.S. Pat. No. 8,617,467 wherein a solution of 1.0% of itraconazole nanosuspension is obtained, the solution containing 0.1% of poloxamer 188, 0.1% of deoxycholate and 2.2% of glycerol. At the temperature of 121° C. used for the thermal sterilization with steam under pressure, the solution becomes turbid (the cloud point of poloxamer 188 is 110° C.) and the nanosuspension is decomposed; thus, to obtain a sterile suspension, equipment is provided that can provide a pressure of 0.25 to 1500 MPa at an operating temperature of 121° C., wherein the recommended pressure is 700 MPa.

The disadvantages of this method are the high cost of the equipment and the small lots of the sterile suspension which leads to high production costs.

The closest analogue of the invention is the method disclosed in the RU patent No. 2157241, wherein a proxanol solution is dissolved in pyrogen-free water in a concentration of 10-15%, then the solution is saturated with carbon dioxide for 30-40 minutes lowering the pH of the solution to 5-6, then the solution is filtered through a membrane filter with pores of 0.22 μm in an atmosphere of carbon dioxide to increase the level of sterility, the stoppered vials with the proxanol solution of 200 and 400 ml are autoclaved under the pressure of 1.1-1.2 kg/cm$^2$ which corresponds to the temperature of 121.1-122.6° C. for 12-15 minutes, the solution is cooled, and then it is warmed for 12-16 hours under the temperature 65-75° C.

The disadvantages of the method are as follows: the pH of the solution is controlled only by saturating it with carbon dioxide; filtering the solution in an atmosphere of carbon dioxide increases the cost of the production of the solution; saturating the solution with carbon dioxide makes it difficult to add, for example, glucose to the solution; using the thermal sterilization with steam under the pressure (1.1-1.2 kg/cm$^2$) leads to high rate of gel formation which does not disappear for 24 hours or longer; cooling the solution and re-heating it to 65-75° C. are energy-consuming processes that do not ensure additional sterility of the solution.

The object of the present invention is to provide a technologically more simple method for obtaining a sterile solution containing a poloxamer, wherein a thermal sterilization method with steam under pressure is used, so that the achievement of the technical result which consists in reducing the time of recovering the poloxamer solution after the gel formation and the time of the thermal sterilization process is ensured.

The object is achieved by providing a thermal method for sterilizing aqueous poloxamer solutions, the method including:

dissolving a poloxamer in water for injection;

performing a sterilizing filtration of the aqueous poloxamer solution simultaneously with filling sterile containers with the filtered poloxamer solution;

sealing the containers containing the poloxamer solution;

applying a thermal sterilization with steam under pressure to the containers containing the poloxamer solution, and cooling the containers, wherein the thermal sterilization of the containers containing the poloxamer solution with steam under pressure is performed under a pressure between 82.4 and 107.8 kPa.

The sterilizing filtration of the aqueous poloxamer solution before it is dispensed into sterile containers is intended to increase the level of sterility.

Due to the reduction of the sterilization pressure from 107.9-117.7 kPa to 82.4-107.8 kPa, the time of recovering the solution after the gel formation was reduced from 24 hours and more to 20-30 minutes.

It is reasonable to cool the containers containing the poloxamer solution to a temperature of 30-40° C. for at least 2 hours.

The cooling of the containers is performed by reducing the steam pressure in a sterilizer for at least 2 hours after the sterilization process is completed before reaching a temperature of 30-40° C. which is controlled by a pressure and temperature sensor.

In a preferred embodiment of the method according to the present invention, the thermal sterilization with steam under pressure is applied to the containers containing 2 to 100 ml of the poloxamer solution for 8-10 minutes.

In another preferred embodiment of the method according to the present invention, the thermal sterilization with steam under pressure is applied to the containers containing 100 to 400 ml of the poloxamer solution for 12 minutes.

Preferably, sterile ampoules or vials are used as the containers.

Preferably, the vials containing the poloxamer solution are sealed by stoppering them with sterile stoppers, covering the vials with sterile aluminium caps and further rolling the caps on.

Preferably, the ampoules containing the poloxamer solution are sealed by sealing them off.

In yet another preferred embodiment, the concentration of the poloxamer in the solution is between 0.1 wt %/1 and 40 wt %/1.

To obtain finished dosage forms of drugs, concentrations of the poloxamer in the solution are typically between 0.1 wt %/1 and 20% wt %/1.

During preparation of drug substances, it is economically reasonable to use concentrations of the poloxamer in the solution between 4 wt %/1 and 40 wt %/1.

Preferably, the poloxamer is dissolved in the water for injections at a temperature of the water between 5 and 25° C. which is determined by the property of poloxamers to dissolve easily in this temperature range of the water.

Preferably, sodium chloride is further added to the aqueous poloxamer solution.

Preferably, potassium chloride is further added to the aqueous poloxamer solution.

In a preferred embodiment, the shelf life of the obtained poloxamer solution is 3 years.

The sterile solutions obtained by the claimed method can be used as drugs, as well as substances for producing drugs, for example, based on perfluoroorganic emulsions.

EMBODIMENTS OF THE METHOD

Example 1. Preparation of a Sterile Aqueous Solution Containing 16% of the Poloxamer of Emuxol-268 of Grade "A"

A metal reservoir with a capacity of 40 liters is filled with 15 liters of water for injection the temperature of which is 7° C., and is filled portionwise with 4.0 kg of the poloxamer. The contents of the reservoir are stirred with a laboratory mixer of a PW type having a "ш"-shaped stirring arm (the rotary speed of the stirring arm is in the range of 500÷700 rpm) until the poloxamer is completely dissolved. The volume of the poloxamer solution is adjusted with the water for injections of the same temperature to 25 liters.

The sterilizing filtration is performed in aseptic conditions. The prepared poloxamer solution is filtered at a pressure of 68.6-147.1 kPa through a sterile hydrophilic membrane filter with a pore diameter of 0.2-0.22 μm. The poloxamer solution is dispensed simultaneously with the sterilizing filtration: 400 ml of the filtered poloxamer solution is fed directly to each of the sterile glass vials that have a volume of 450 ml and used for infusion preparations, then the vials containing the poloxamer solution are stoppered with sterile stoppers, and covered and rolled with sterile aluminium caps. The sterilization of the poloxamer solution in the vials is performed in a steam sterilizer VK-75 at a pressure of 88.3 kPa for 12 minutes. After the completion of the process of the thermal sterilization with steam under pressure, the vials containing the poloxamer solution are cooled to 35° C. for 2.5 hours. The insignificant gel formation of the poloxamer solution disappears after 30 minutes. The poloxamer solution treated this way is tested for sterility and pyrogenicity.

The test results are shown in Table 1.

TABLE 1

The comparison table of the testing of the poloxamer solution for sterility and pyrogenicity in the process of production

| Name of test object | Pyrogenicity | | Sterility | |
|---|---|---|---|---|
| | Requirement of normative documentation | Analysis results | Requirement of normative documentation | Analysis results |
| Poloxamer solution, 16%, 400 ml | Must be pyrogen-free | Pyrogen-free | Must be sterile | Sterile |

Example 2. Preparation of a Sterile Aqueous Solution Containing 1% of the Poloxamer of Lutrol F68

A metal reservoir with a capacity of 40 liters is filled with 16 liters of water for injection the temperature of which is 20° C., and then is filled portionwise with 0.25 kg of the poloxamer. The contents of the reservoir are stirred with a laboratory mixer of a PW type having a "ш"-shaped stirring arm (the rotary speed of the stirring arm is in the range of 500÷700 rpm) until the poloxamer is completely dissolved. The volume of the poloxamer solution is adjusted with the water for injections of the same temperature to 25 liters.

The sterilizing filtration is performed in aseptic conditions. The prepared poloxamer solution is filtered at a pressure of 68.6-147.1 kPa through a sterile hydrophilic membrane filter with a pore diameter of 0.2-0.22 μm. The poloxamer solution is dispensed simultaneously with the sterilizing filtration: 200 ml of the filtered poloxamer solution is fed directly to each of the sterile glass vials that have a volume of 250 ml and used for infusion preparations, then the vials containing the poloxamer solution are stoppered with sterile stoppers, and covered and rolled with sterile aluminium caps. The sterilization of the poloxamer solution in the vials is performed in a steam sterilizer VK-75 at a pressure of 98.1 kPa for 12 minutes. After the completion of the process of the thermal sterilization with steam under pressure, the vials containing the poloxamer solution are cooled to 30° C. for 2 hours and 10 minutes. The insignificant gel formation of the poloxamer solution disappears after 20 minutes. The poloxamer solution treated this way is tested for sterility and pyrogenicity.

The test results are shown in Table 2.

TABLE 2

The comparison table of the testing of the poloxamer solution for sterility and pyrogenicity in the process of production

| Name of test object | Pyrogenicity | | Sterility | |
|---|---|---|---|---|
| | Requirement of normative documentation | Analysis results | Requirement of normative documentation | Analysis results |
| Poloxamer solution, 1%, 200 ml | Must be pyrogen-free | Pyrogen-free | Must be sterile | Sterile |

Example 3. Preparation of a Sterile Aqueous Solution Containing 28% of the Poloxamer of Emuxol-268 of Grade "A"

A metal reservoir with a capacity of 40 liters is filled with 16 liters of water for injection the temperature of which is 11° C., and is filled portionwise with 7.0 kg of the poloxamer. The contents of the reservoir are stirred with a laboratory mixer of a PW type having a "Ш"-shaped stirring arm (the rotary speed of the stirring arm is in the range of 500÷700 rpm) until the poloxamer is completely dissolved. The volume of the poloxamer solution is adjusted with the water for injections of the same temperature to 25 liters.

The sterilizing filtration is performed in aseptic conditions. The prepared poloxamer solution is filtered at a pressure of 68.6-147.1 kPa through a sterile hydrophilic membrane filter with a pore diameter of 0.2-0.22 μm. The poloxamer solution is dispensed simultaneously with the sterilizing filtration: 200 ml of the filtered poloxamer solution is fed directly to each of the sterile glass vials that have a volume of 250 ml and used for infusion preparations, then the vials containing the poloxamer solution are stoppered with sterile stoppers, and covered and rolled with sterile aluminium caps. The sterilization of the poloxamer solution in the vials is performed in a steam sterilizer VK-75 at a pressure of 83.4 kPa for 12 minutes. After the completion of the process of the thermal sterilization with steam under pressure, the vials containing the poloxamer solution are cooled to 40° C. for 3 hours. Gel formation of the poloxamer solution was not observed. The poloxamer solution treated this way is tested for sterility and pyrogenicity.

The test results are shown in Table 3.

TABLE 3

The comparison table of the testing of the poloxamer solution for sterility and pyrogenicity in the process of production

| Name of test object | Pyrogenicity | | Sterility | |
|---|---|---|---|---|
| | Requirement of normative documentation | Analysis results | Requirement of normative documentation | Analysis results |
| Poloxamer solution, 28%, 200 ml | Must be pyrogen-free | Pyrogen-free | Must be sterile | Sterile |

Example 4. Preparation of a Sterile Aqueous Solution Containing 6% of the Poloxamer of Emuxol-268 of Grade "A" and 0.9% of Sodium Chloride A metal reservoir with a capacity of 40 liters is filled with 15 liters of water for injection the temperature of which is 18° C., and is filled portionwise with 1.5 kg of the poloxamer. The contents of the reservoir are stirred with a laboratory mixer of a PW type having a "Ш"-shaped stirring arm (the rotary speed of the stirring arm is in the range of 500÷700 rpm) until the poloxamer is completely dissolved. 0.36 kg of sodium chloride is added to the resulting solution and stirred. The volume of the poloxamer solution is adjusted with the water for injections of the same temperature to 25 liters.

The sterilizing filtration is performed in aseptic conditions. The prepared poloxamer solution is filtered at a pressure of 68.6-147.1 kPa through a sterile hydrophilic membrane filter with a pore diameter of 0.2-0.22 μm. The poloxamer solution is dispensed simultaneously with the sterilizing filtration: 10 ml of the filtered poloxamer solution is fed directly to each of the glass ampoules that have a capacity of 12 ml, and then the ampoules are sealed off. The sterilization of the poloxamer solution in the ampoules is performed in a steam sterilizer VK-75 at a pressure of 85.0 kPa for 8 minutes. After completion of the process of the thermal sterilization with steam under pressure, the ampoules containing the poloxamer solution are cooled to 32° C. for 2 hours. Gel formation of the poloxamer solution was not observed. The poloxamer solution treated this way is tested for sterility and pyrogenicity.

The test results are shown in Table 4.

TABLE 4

The comparison table of the testing of the poloxamer solution for sterility and pyrogenicity in the process of production

| Name of test object | Pyrogenicity | | Sterility | |
|---|---|---|---|---|
| | Requirement of normative documentation | Analysis results | Requirement of normative documentation | Analysis results |
| Poloxamer solution, 10 ml, 6% with 0.9% of sodium chloride | Must be pyrogen-free | Pyrogen-free | Must be sterile | Sterile |

Example 5. Preparation of a Sterile Aqueous Solution Containing 16% of the Poloxamer of Emuxol-268 of Grade "A" at a Pressure of 82.0 kPa Without Preliminary Sterilizing Filtration A metal reservoir with a capacity of 40 liters is filled with 17 liters of water for injection the temperature of which is 7° C., and is filled portionwise with 4.0 kg of the poloxamer. The contents of the reservoir are stirred with a laboratory mixer of a PW type having a "Ш"-shaped stirring arm (the rotary speed of the stirring arm is in the range of 500÷700 rpm) until the poloxamer is completely dissolved. The volume of the poloxamer solution is adjusted with the water for injections of the same temperature to 25 liters.

400 ml of the poloxamer solution is dispensed simultaneously into each of the sterile glass vials that have a volume of 450 ml and used for infusion preparations, then the vials containing the poloxamer solution are stoppered with sterile stoppers, and covered and rolled with sterile aluminium caps. The sterilization of the poloxamer solution in the vials is performed in a steam sterilizer VK-75 at a pressure of 82.0 kPa for 12 minutes. After the completion of the process of the thermal sterilization with steam under pressure, the vials containing the poloxamer solution are cooled to 34° C. for 2 hours and 10 minutes. The insignificant gel formation of the poloxamer solution disappears after 20 minutes. The poloxamer solution treated this way is tested for sterility and pyrogenicity.

The test results are shown in Table 5.

TABLE 5

The comparison table of the testing of the poloxamer solution for sterility and pyrogenicity in the process of production

| | Pyrogenicity | | Sterility | |
| --- | --- | --- | --- | --- |
| Name of test object | Requirement of normative documentation | Analysis results | Requirement of normative documentation | Analysis results |
| Poloxamer solution, 16%, 400 ml, at a pressure of 82.0 kPa without preliminary sterilizing filtration | Must be pyrogen-free | Pyrogen-free | Must be sterile | Not sterile |

Example 6. Preparation of a Sterile Aqueous Solution Containing 6% of the Poloxamer of Emuxol-268 of Grade "A" and 0.9% of Sodium Chloride at a Pressure of 108.0 kPa A metal reservoir with a capacity of 40 liters is filled with 15 liters of water for injection the temperature of which is 18° C., and is filled portionwise with 1.5 kg of the poloxamer. The contents of the reservoir are stirred with a laboratory mixer of a PW type having a "ш"-shaped stirring arm (the rotary speed of the stirring arm is in the range of 500÷700 rpm) until the poloxamer is completely dissolved. 0.36 kg of sodium chloride is added to the resulting solution and stirred. The volume of the poloxamer solution is adjusted with the water for injections of the same temperature to 25 liters.

The sterilizing filtration is performed in aseptic conditions. The prepared poloxamer solution is filtered at a pressure of 68.6-147.1 kPa through a sterile hydrophilic membrane filter with a pore diameter of 0.2-0.22 μm. The poloxamer solution is dispensed simultaneously with the sterilizing filtration: 10 ml of the filtered poloxamer solution is fed directly to each of the glass ampoules that have a capacity of 12 ml, and then the ampoules are sealed off. The sterilization of the poloxamer solution in ampoules is performed in a steam sterilizer VK-75 at a pressure of 108.0 kPa for 8 minutes. After completion of the process of the thermal sterilization with steam under pressure, the ampoules containing the poloxamer solution are cooled to 35° C. for 2 hours. The gel formation of the poloxamer solution disappears after 25 hours. The poloxamer solution treated this way is tested for sterility and pyrogenicity.

The test results are shown in Table 6.

TABLE 6

The comparison table of the testing of the poloxamer solution for sterility and pyrogenicity in the process of production

| | Pyrogenicity | | Sterility | |
| --- | --- | --- | --- | --- |
| Name of test object | Requirement of normative documentation | Analysis results | Requirement of normative documentation | Analysis results |
| Poloxamer solution, 10 ml, 6% with 0.9% of sodium chloride at a pressure of 108.0 kPa | Must be pyrogen-free | Pyrogen-free | Must be sterile | Sterile |

Thus, provided is a technologically more simple method for obtaining a sterile solution containing a poloxamer, wherein a thermal sterilization method with steam under pressure is used, so that the achievement of the technical result which consists in reducing the time of recovering the poloxamer solution after the gel formation and the time of the thermal sterilization process is ensured. According to the invention, the obtained aqueous solutions containing, in particular, the poloxamer are subjected to preliminary sterilizing filtration and thermal sterilization with steam in conditions that ensure sterility and the absence of pyrogenic impurities, wherein the cooling time is controlled to preserve the properties of the poloxamer, as evidenced by the transparency of the solution.

The invention claimed is:

1. A thermal method for sterilizing aqueous poloxamer solutions, the method including:
    dissolving a poloxamer in water for injection;
    performing a sterilizing filtration of the aqueous poloxamer solution simultaneously with filling sterile containers with the filtered poloxamer solution;
    sealing the containers containing the poloxamer solution; and
    applying a thermal sterilization with steam under pressure to the containers containing the poloxamer solution, and cooling the containers,
    characterized in that the thermal sterilization of the containers containing the poloxamer solution with steam under pressure is performed under a pressure between 82.4 and 107.8 kPa, and in that the containers containing the poloxamer solution are cooled to a temperature of 30-40° C. for at least 2 hours.

2. The method according to claim 1, characterized in that the thermal sterilization with steam under pressure is applied to the containers containing 2 to 100 ml of the poloxamer solution for 8-10 minutes.

3. The method according to claim 1, characterized in that containers containing 100 to 400 ml of the poloxamer solution are subjected to the thermal sterilization with steam under pressure for 12 minutes.

4. The method according to claim 1, characterized in that sterile ampoules or vials are used as the containers.

5. The method according to claim 4, characterized in that the vials containing the poloxamer solution are sealed by stoppering them with sterile stoppers, covering the vials with sterile aluminium caps and further rolling the caps on.

6. The method according to claim 4, characterized in that the ampoules containing the poloxamer solution are sealed by sealing them off.

7. The method according to claim 1, characterized in that the concentration of the poloxamer in the solution is between 0.1 wt %/1 and 40 wt %/1.

8. The method according to claim 1, characterized in that the poloxamer is dissolved in the water for injections at a temperature of the water between 5 and 25° C.

9. The method according to claim 1, characterized in that sodium chloride is further added to the aqueous poloxamer solution.

10. The method according to claim 1, characterized in that potassium chloride is further added to the aqueous poloxamer solution.

* * * * *